US006936265B2

(12) United States Patent
Bleckmann et al.

(10) Patent No.: US 6,936,265 B2
(45) Date of Patent: Aug. 30, 2005

(54) PREPARATIONS OF THE W/O EMULSION TYPE WITH AN INCREASED WATER CONTENT BASED ON LOW-VISCOSITY, READILY SPREADABLE LIPID COMPONENTS, ADDITIONALLY COMPRISING ONE OR MORE ALKYLMETHICONE COPOLYOLS AND/OR ALKYLDIMETHICONE COPOLYOLS

(75) Inventors: Andreas Bleckmann, Ahrensburg (DE); Rainer Kröpke, Schenefeld (DE)

(73) Assignee: Beiersdorf Aktiengesellschaft, Hamburg (DE)

( * ) Notice: Subject to any disclaimer, the term of this patent is extended or adjusted under 35 U.S.C. 154(b) by 55 days.

(21) Appl. No.: 09/963,161

(22) Filed: Sep. 26, 2001

(65) Prior Publication Data

US 2002/0106386 A1 Aug. 8, 2002

(30) Foreign Application Priority Data

Sep. 30, 2000 (DE) .......................... 100 48 683

(51) Int. Cl.$^7$ ............................. A61K 7/00; A61K 7/06; C09K 3/00
(52) U.S. Cl. ..................... 424/401; 424/70.1; 516/21
(58) Field of Search ................ 424/401, 70.1; 516/21

(56) References Cited

U.S. PATENT DOCUMENTS 5,326,566 A * 7/1994 Parab .......................... 424/401
5,378,455 A * 1/1995 Kealey et al. ................ 424/73
6,139,824 A * 10/2000 Ribery et al. ................ 424/65
2001/0012860 A1 * 8/2001 Bleckmann et al. .......... 516/21

FOREIGN PATENT DOCUMENTS

| DE | 692 10 515 T2 | 11/1996 |
| DE | 198 26 750 A1 | 12/1999 |
| DE | 199 33 463 A1 | 1/2000 |
| DE | 198 44 261 A1 | 3/2000 |
| DE | 198 52 212 A1 | 5/2000 |

OTHER PUBLICATIONS

Wenninger et al. 'International Cosmetic Ingredient dictionary and Handbook,' 1997, p. 406.*

* cited by examiner

Primary Examiner—Shengjun Wang
(74) Attorney, Agent, or Firm—Norris McLaughlin & Marcus PA

(57) ABSTRACT

Water-in-oil emulsions
(a) having a water phase content of at least 80% by weight, based on the total weight of the emulsions,
(b) in which the lipid phase comprises at least one lipid with a viscosity of less than 15 mPa·s (at 25° C.), which has a spreading value of at least 700 mm$^2$/10 minutes (at 25° C.),
(c) at least one interface-active substance chosen from the group of alkylmethicone copolyols and/or alkyldimethicone copolyols,
(d) if desired also comprising one or more cationic, nonionic and/or anionic polymers, preferably in concentrations of from 0.01 to 10% by weight, preferably 0.1 to 5% by weight, particularly preferably 0.25 to 1% by weight.

10 Claims, No Drawings

PREPARATIONS OF THE W/O EMULSION TYPE WITH AN INCREASED WATER CONTENT BASED ON LOW-VISCOSITY, READILY SPREADABLE LIPID COMPONENTS, ADDITIONALLY COMPRISING ONE OR MORE ALKYLMETHICONE COPOLYOLS AND/OR ALKYLDIMETHICONE COPOLYOLS

This application claims foreign priority of Germany 100 48 683.5, filed Sep. 30, 2000.

The present invention relates to cosmetic and dermatological preparations, in particular those of the water-in-oil type, to processes for their preparation and to their use for cosmetic and medicinal purposes.

The human skin is man's largest organ and performs a number of vital functions. Having an average area of about 2 m² in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or restore the skin's natural function as a barrier against environmental influences (e.g. dirt, chemicals, microorganisms) and against the loss of endogenous substances (e.g. water, natural fats, electrolytes), and also to assist its horny layer in its natural regeneration ability in cases of existing damage.

If the barrier properties of the skin are impaired, increased resorption of toxic or allergenic substances or attack by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally taken to mean heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic character being determined here by the oil.

The person skilled in the art is of course aware of a large number of ways to formulate stable W/O preparations for cosmetic or dermatological use, for example in the form of creams and ointments which can be spread in the range from room temperature to skin temperature, or as lotions and milks, which are more likely flowable in this temperature range. However, there are only a few formulations in the prior art which are of sufficiently low-viscosity that they would, for example, be sprayable.

In addition, low-viscosity preparations of the prior art frequently have the disadvantage that they are unstable, and are limited to a narrow field of application or a limited choice of feed materials. Low-viscosity products in which, for example, strongly polar oils—such as the plant oils otherwise frequently used in commercially available products—are sufficiently stabilized are therefore currently not on the market.

The term "viscosity" means the property of a liquid to resist the mutual laminar displacement of two neighboring layers (internal friction). This so-called dynamic viscosity is nowadays defined according to $\eta=\tau/D$ as the ratio of shear stress to the velocity gradient perpendicular to the direction of flow. For Newtonian liquids, $\eta$ is a material constant having the SI unit Pascal second (Pa·s) at a given temperature.

The quotient $\nu=\eta/\rho$ from the dynamic viscosity $\eta$ and the density $\rho$ of the liquid is referred to as the kinematic viscosity $\nu$ and is given in the SI unit m²/s.

Fluidity ($\phi$) is the inverse of viscosity ($\phi=1/\eta$). In the case of ointments and the like, the use value is inter alia codetermined by the so-called tack. The tack of an ointment or ointment base or the like means its property to draw threads of varying lengths when a small sample is removed; accordingly, a distinction is made between short- and long-stretch substances.

Whilst the graphical representation of the flow behavior of Newtonian liquids at a given temperature produces a straight line, in the case of so-called non-Newtonian liquids considerable deviations often arise, depending on the velocity gradient D (shear rate $\gamma$) or the shear stress $\tau$. In these cases, the so-called apparent viscosity can be determined which, although it does not obey the Newtonian equation, can be used to determine the true viscosity values by graphical methods.

Falling-body viscometry is suitable only for investigating Newtonian liquids and gases. It is based on Stokes's law, according to which, for the falling of a sphere through a liquid which flows around it, the dynamic viscosity $\eta$ can be determined from $$\eta = \frac{2r^2(\rho_K - \rho_{Fl}) \cdot g}{9 \cdot v}$$

where
r=radius of the sphere, v=fall velocity, $\rho_K$=density of the sphere, $\rho_{Fl}$=density of the liquid and g=acceleration of the fall.

The viscosity values of the preparations and individual substances listed within the scope of the present disclosure were determined using a Viscotester VT 02 type viscometer from the company Haake.

W/O emulsions with a high water content and a low viscosity which moreover have storage stability, as is required for marketable products, can only be formulated with difficulty according to the prior art. Accordingly, the supply of such formulations is extremely small. Nevertheless, such formulations could offer the consumer hitherto unknown cosmetic effects.

An object of the present invention was to provide preparations which have a very low viscosity and do not have the disadvantages of the prior art.

Another object of the present invention was to provide preparations which can be laden with a high content of water-soluble and/or water-miscible substances having cosmetic or dermatological effectiveness, without impairing the galenical quality or other properties of the preparations.

Surprisingly, it has been found that water-in-oil emulsions
(a) having a water phase content of at least 80% by weight, based on the total weight of the emulsions,
(b) in which the lipid phase comprises at least one lipid with a viscosity of less than 15 mPa·s (at 25° C.), which has a spreading value of at least 700 mm²/10 minutes (at 25° C.),
(c) at least one interface-active substance chosen from the group of alkylmethicone copolyols and/or alkyldimethicone copolyols,
(d) if desired also comprising one or more cationic, nonionic and/or anionic polymers, preferably in concentrations of from 0.01 to 10% by weight, preferably 0.1 to 5% by weight, particularly preferably 0.25 to 1% by weight,
are able to achieve these objects.

According to the invention, the silicone emulsifiers can advantageously be chosen from the group of interface-active substances from the group of alkylmethicone copolyols and/or alkyldimethicone copolyols, in particular from the group of compounds characterized by the following chemical structure:

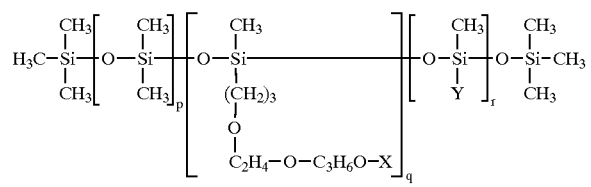

in which X and Y, independently of one another, are chosen from the group H, and of branched and unbranched alkyl groups, acyl groups and alkoxy groups having 1–24 carbon atoms, p is a number from 0–200, q is a number from 1–40, and r is a number from 1–100.

One example of silicone emulsifiers which are to be used particularly advantageously for the purposes of the present invention are dimethicone copolyols, which are sold by the company Th.Goldschmidt AG under the trade names ABIL® B 8842, ABIL® B 8843, ABIL® B 8847, ABIL® B 8851, ABIL® B 8852, ABIL® B 8863, ABIL® B 8873 and ABIL® B 88183.

Another example of interface-active substances which are to be used particularly advantageously for the purposes of the present invention is cetyldimethicone copolyol, which is sold by the company Th.Goldschmidt AG under the trade name ABIL® EM 90.

A further example of interface-active substances to be used particularly advantageously for the purposes of the present invention is the cyclomethiconedimethicone copolyol, which is sold by the company Th.Goldschmidt AG under the trade name ABIL® EM 97.

In addition, the emulsifier laurylmethicone copolyol has proven to be very particularly advantageous and is available under the trade name Dow Corning® 5200 Formulation Aid from the company Dow Corning Ltd.

The total amount of silicone emulsifiers used according to the invention in the cosmetic or dermatological preparations according to the invention is advantageously chosen from the range 0.1–10.0% by weight, preferably 0.5–5.0% by weight, based on the total weight of the preparations.

Although it is known that W/O emulsions can be produced using emulsifiers of the type described above, the known prior art was nevertheless unable to indicate the route to the present invention.

It had therefore not been foreseen by the person skilled in the art that the preparations according to the invention would have better effectiveness as moisture-donating preparations, would be easier to formulate, would better promote skin smoothing, would be characterized by better care action, would better serve as vehicles for cosmetic and medicinal-dermatological active ingredients would have better sensory properties, such as, for example, the ability to be distributed on the skin or the ability to be absorbed into the skin, would have higher stability against decomposition in oil and water phases and would be characterized by better biocompatibility than the preparations of the prior art.

It is possible and advantageous to choose the water content of the W/O emulsions according to the invention to be significantly more than 80% by weight, in particular more than 85% by weight, in each case based on the total weight of the preparations.

Spreading is the often desired, but in other situations also often undesired property based predominantly on capillary forces of low-viscosity oils to be distributed in a thin layer particularly readily on substrates or else on the skin. This may be advantageous in skincare. This property may have an adverse effect during the packaging of such oils or preparations containing them. One measure of the spreadability is the spreading coefficient, which, for example, in the case of antifoams and foam preventatives, assumes particularly high values.

Barry and Grace developed a method to determine the spreading behavior (J. Pharmac. Sci. 61, 335 [1972]) and Beyer developed a model test system to test spreading behavior (Arch. Pharm. [Weinh.] 310, 729 [1977]; Chem. Abstr. 88, No. 12–79017 [1978]). The spreading of ointments on the model is also reported by Beyer in Arch. Pharm. 310, 473 and 858 (1977); Zbl. Pharm. 118, 51 (1979). The spreadability of various liquid auxiliaries based on fats or fat-like substances has been reported by Pascale et.al. (Cosmet. Toiletries 100, No. 10, 75 [1985]).

The unit of the spreading coefficient is that of the quotient of the spreading area over which spreading takes place, and the spreading time in which spreading takes place. It is usually given in [mm²/10 minutes].

For the purposes of the present disclosure, the expression "lipids" is sometimes used as a generic term for fats, oils, waxes and the like, said expression being entirely familiar to the person skilled in the art. The terms "oil phase" and "lipid phase" are also used synonymously.

Preparations according to the invention preferably comprise up to 35% by weight of a lipid phase.

According to the teaching presented herein, W/O emulsions are advantageously obtainable whose viscosity at 25° C. is less than 5 000 mPa·s (=millipascal seconds), in particular less than 2 500 mPa·s, preferably less than 1 500 mPa·s (measured using Viscotester VT-02, Haake).

The oils used according to the invention are advantageously chosen from the group of substances listed in the following table:

TABLE 1

| Trade name | Name analogous to INCI | Viscosity mPas mPa·s | Spreadability (20 μl/red band filter) mm²/10 min |
|---|---|---|---|
| Solvent IH | Isohexadecane | 8 | 990 |
|  | Isoeicosane | 12 | 800 |
| Cegesoft ® C24 | Octyl palmitate | 11 | 910 |
|  | Isopropyl stearate | 9 | 910 |
| Estol ® 1540 EHC | Octyl cocoate | 10 | 930 |
| Finsolv ® TN | $C_{12-15}$-Alkyl benzoate | 14 | 730 |
| Cetiol ® OE | Dicaprylyl ether | 8 | 1020 |
| DUB DNPG | Neopentyl glycol diheptanoate | 13 | 830 |
| Miglyol ® 840 | Propylene glycol dicaprylate/dicaprate | 12 | 855 |
| DC Fluid 345 | Cyclomethicone | 5 | 770 |
|  | Isopropyl palmitate | 7.1 | 1590 |
| Cetiol ® B | Dibutyl adipate | 5.5 | 935 |
| DUB VCI 10 | Isodecyl neopentanoate | 3.9 | 962 |
| Cetiol ® CC | Dicaprylyl carbonate | 7.26 | 875 |
| Cetiol ® S | Dioctylcyclohexane | 14.41 | 723 |
|  | Dihexyl carbonate | 3.8 | 1056 |
|  | Dihexyl ether | 1.87 | 1174 |
| Ecolane ® 130 | Cycloparaffin | 5.22 | 908 |
| Softcutol ® O | Ethoxydiglycol oleate | 13.07 | 804 |
| Transcutol ® CG | Ethoxy diglycol | 4.14 | 999 |
| Dermofeel ® BGC | Butylene glycol caprylate/caprate | 12 | 800 |
| Prisorine ® 2036 | Octyl isostearate | 15 | 800 |
| Tegosoft ® SH | Stearyl heptanoate | 13 | 755 |
| Tegosoft ® DC | Decyl cocoate | 10.3 | 788 |
| Transcutol ® P | Ethoxy diglycol | 4.27 | 962 |
| Arlasolv ® DMI | Dimethyl isosorbide | 10 | 880 |

Particular preference is given to dicaprylyl carbonate, dibutyl adipate, octyl cocoate (=ethylhexyl cocoate), octyl palmitate (=ethylhexyl palmitate), octyl isostearate (=ethylhexyl isostearate).

Accordingly, it is preferred according to the invention to choose a content of the lipid or of the lipids having a viscosity of less than 15 mPa·s (at 25° C.) which has a spreading value of at least 700 mm²/10 minutes (at 25° C.) in the lipid phase according to the invention of at least about 50% by weight, advantageously at least about 75% by weight, particularly advantageously at least 80% by weight, in each case based on the total lipid phase.

The aqueous phase of the preparations according to the invention may advantageously comprise alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol.

A particular advantage of the present invention is that it permits the use of high concentrations of polyols, in particular glycerol.

Emulsions according to the invention preferably comprise one or more hydrocolloids.

"Hydrocolloid" is the technical abbreviation for the more accurate name "hydrophilic colloid". Hydrocolloids are macromolecules which have a largely linear structure and have intermolecular forces of interaction which permit secondary and primary valence bonds between the individual molecules and thus the formation of a network-like structure. Some of them are water-soluble natural or synthetic polymers which form gels or viscous solutions in aqueous systems. They increase the viscosity of the water by either bonding water molecules (hydration), or else by absorbing and encapsulating the water into their interwoven macromolecules, at the same time restricting the mobility of the water. Such water-soluble polymers represent a large group of chemically very different natural and synthetic polymers whose common feature is their solubility in water or aqueous media. A prerequisite for this is that these polymers have a number of hydrophilic groups sufficient for the solubility in water and are not too strongly crosslinked. The hydrophilic groups may be nonionic, anionic or cationic in nature, for example as follows:

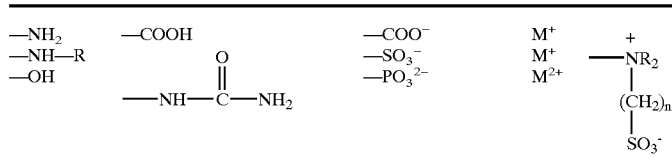

-continued

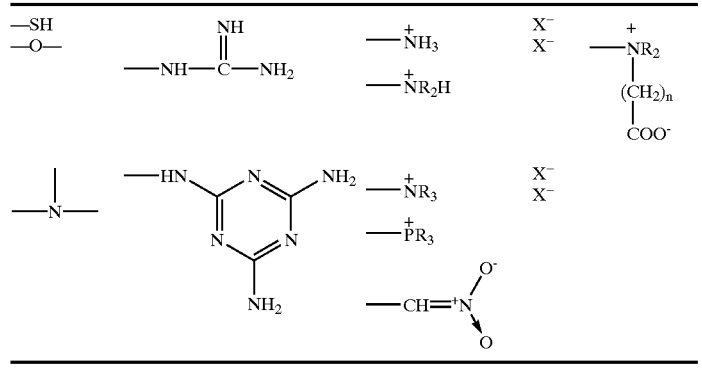

The group of cosmetically and dermatologically relevant hydrocolloids can be divided as follows:
- organic, natural compounds, such as, for example, agar agar, carrageen, tragacanth, gum arabic, alginates, pectins, polyoses, guar flour, carob bean flour, starch, dextrins, gelatin, casein,
- organic, modified natural substances, such as, for example, carboxymethylcellulose and other cellulose ethers, hydroxyethyl- and -propylcellulose and the like,
- organic, fully synthetic compounds, such as, for example, polyacrylic and polymethacrylic compounds, vinyl polymers, polycarboxylic acids, polyethers, polyimines, polyamides,
- inorganic compounds, such as, for example, polysilicic acids, clay minerals, such as montmorillonite, zeolites, silicas.

Examples of hydrocolloids which are preferred according to the invention are methylcelluloses, which is the name for the methyl ethers of cellulose. They are characterized by the following structural formula;

Structural formula I

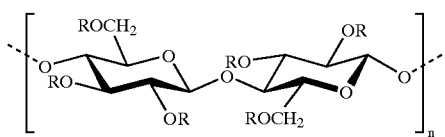

in which R can be a hydrogen or a methyl group.

Particularly advantageous for the purposes of the present invention are the cellulose mixed ethers, which are generally likewise referred to as methylcelluloses, which contain, in addition to a dominating content of methyl groups, additionally 2-hydroxyethyl, 2-hydroxypropyl and 2-hydroxybutyl groups. Particular preference is given to (hydroxypropyl)methylcelluloses, for example those available under the trade name Methocel E4M from Dow Chemical Comp.

Also advantageous according to the invention is sodium carboxymethylcellulose, the sodium salt of the glycolic ether of cellulose, for which R in structural formula I can be a hydrogen and/or $CH_2$—COONa. Particular preference is given to the sodium carboxymethylcellulose available under the trade name Natrosol Plus 330 CS from Aqualon and also referred to as cellulose gum.

For the purposes of the present invention, preference is also given to xanthan (CAS No. 11138-66-2), also called xanthan gum, which is an anionic heteropolysaccharide which is generally formed by fermentation from maize sugar and is isolated as the potassium salt. It is produced by *Xanthomonas campestris* and a few other species under aerobic conditions with a molecular weight of $2 \times 10^6$ to $24 \times 10^6$. Xanthan is formed from a chain having β-1,4-bonded glucose (cellulose) with side chains. The structure of the subgroups consists of glucose, mannose, glucuronic acid, acetate and pyruvate. Xanthan is the name for the first microbial anionic heteropolysaccharide. It is produced by *Xanthomonas campestris* and a few other species under aerobic conditions with a molecular weight of $2-15 \times 10^6$. Xanthan is formed from a chain having β-1,4-bonded glucose (cellulose) with side chains. The structure of the subgroups consists of glucose, mannose, glucuronic acid, acetate and pyruvate. The number of pyruvate units determines the viscosity of the xanthan. Xanthan is produced in two-day batch cultures with a yield of 70–90%, based on carbohydrate used. In this connection, yields of 25–30 g/l are achieved. After the culture has been killed, work-up is carried out by precipitation with e.g. 2-propanol. Xanthan is then dried and ground.

For the purposes of the present invention, another advantageous gel former is carrageen, a gel-forming extract with a similar structure to agar, of North Atlantic red algae which belong to the Florideae (*Chondrus crispus* and *Gigartina stellata*).

The term carrageen is frequently used for the dried algae product and carrageenan for the extract thereof. The carrageen precipitated from the hot-water extract of the algae is a colorless to sand-colored powder with a molecular weight range from 100 000–800 000 and a sulfate content of about 25%. Carrageen, which is very readily soluble in warm water, forms a thixotropic gel on cooling, even if the water content is 95–98%. The rigidity of the gel is effected by the double helix structure of the carrageen. In the case of carrageenan, three principal constituents are differentiated: the gel-forming κ fraction consists of D-galactose 4-sulfate and 3,6-anhydro-α-D-galactose, having alternate glycoside bonds in the 1,3 and 1,4 positions (agar, in contrast, contains 3,6-anhydro-α-L-galactose). The non-gelling λ fraction is composed of 1,3-glycosidically linked D-galactose 2-sulfate and 1,4-bonded D-galactose 2,6-disulfate radicals and is readily soluble in cold water. τ-Carrageenan, composed of D-galactose 4-sulfate in 1,3 bond and 3,6-anhydro-α-D-galactose 2-sulfate in 1,4 bond, is both water-soluble and also gel-forming. Other types of carrageen are likewise labeled with Greek letters: α, β, γ, μ, ν, ξ, π, ω, χ. The nature of cations which are present ($K^+$, $NH_4^+$, $Na^+$, $Mg^{2+}$, $Ca^{2+}$) also influences the solubility of the carrageens.

The use of chitosan in cosmetic preparations is known per se. Chitosan represents a partially deacylated chitin. This biopolymer has, inter alia, film-forming properties and is characterized by a silky feel on the skin. A disadvantage, however, is its severe stickiness on the skin which occurs in particular—temporarily—during application. In individual cases corresponding preparations may not then be marketable since they are unacceptable to and viewed negatively by the consumer. As is known, chitosan is used, for example, in hair care. It is suitable, to a better degree than the chitin on which it is based, as a thickener or stabilizer and improves the adhesion and water resistance of polymeric films. A representative of the large number of literature references for the prior art is: H. P. Fiedler, "Lexikon der Hilfsstoffe für Pharmazie, Kosmetik und angrenzende Gebiete" [Lexikon of auxiliaries for pharmacy, cosmetics and related fields], third edition 1989, Editio Cantor, Aulendorf, p. 293, keyword "Chitosan".

Chitosan is characterized by the following structural formula:

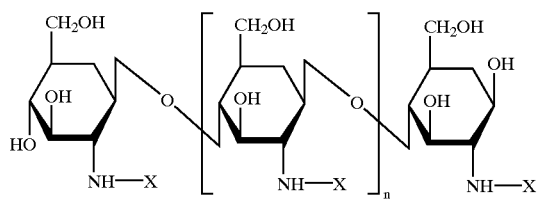

where n assumes values up to about 10 000, and X is either the acetyl radical or hydrogen. Chitosan forms by deacetylation and partial depolymerization (hydrolysis) of chitin, which is characterized by the structural formula:

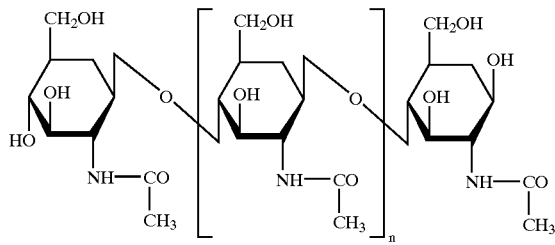

Chitin is an essential constituent of the ecto skeleton ['o χιτων=Greek: integument] of arthropods (e.g. insects, crabs, spiders) and is also found in supporting tissues of other organisms (e.g. molluscs, algae, fungi).

In the region of about pH <6, chitosan is positively charged and in that range is also soluble in aqueous systems. It is incompatible with anionic raw materials. For this reason, to prepare chitosan-containing oil-in-water emulsions, the use of nonionic emulsifiers is appropriate. These are known per se, for example from EP-A 776 657.

Preference is given according to the invention to chitosans with a degree of deacetylation of >25%, in particular >55 to 99% [determined by means of $^1$H-NMR].

It is advantageous to choose chitosans with molecular weights between 10 000 and 1 000 000, in particular those with molecular weights between 100 000 and 1 000 000. [determined by means of gel permeation chromatography].

Polyacrylates are gelling agents likewise to be used advantageously for the purposes of the present invention. Polyacrylates advantageous according to the invention are acrylate-alkyl acrylate copolymers, in particular those chosen from the group of so-called carbomers or carbopols (Carbopol® is actually a registered trademark of B. F. Goodrich Company). In particular, the acrylate-alkyl acrylate copolymers advantageous according to the invention are characterized by the following structure:

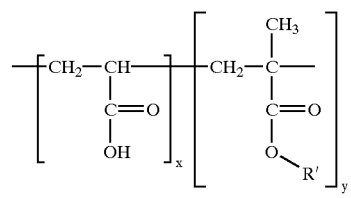

where R' is a long-chain alkyl radical, and x and y represent numbers which symbolize the respective stoichiometric proportion of each of the comonomers.

According to the invention, particular preference is given to acrylate copolymers and/or acrylate-alkyl acrylate copolymers which are available under the trade names Carbopol® 1382, Carbopol® 981 and Carbopol® 5984 from B. F. Goodrich Company.

Also advantageous are copolymers of $C_{10-30}$-alkyl acrylates and one or more monomers of acrylic acid, of methacrylic acid or esters thereof which are crosslinked with an allyl ether of sucrose or an allyl ether of pentaerythritol.

Compounds which carry the INCI name "Acrylates/C 10–30 Alkyl Acrylate Crosspolymer" are advantageous. Particularly advantageous are those available under the trade names Pemulen TR1 and Pemulen TR2 from B. F. Goodrich Company.

The total amount of one or more hydrocolloids in the finished cosmetic or dermatological preparations is advantageously chosen to be less than 1.5% by weight, preferably between 0.1 and 1.0% by weight, based on the total weight of the preparations.

Hydrocolloids from the group of anionic polymers are advantageously chosen for the purposes of the present invention from the group of carbomers as sodium, potassium, TEA and trisamino salts, sodium, potassium hyaluronate, microcrystalline cellulose+cellulose gum, Veegum grades, hectorites, bentonites, laponites, alginates, methacrylates.

Hydrocolloids from the group of nonionic polymers are advantageously chosen for the purposes of the present invention from the group consisting of polyvinylpyrrolidone, hydroxypropylmethylcellulose, polyvinyl alcohol, polyether-1, xanthan gum, hydroxyethylcellulose, cellulose derivatives, starch, starch derivatives, guar gum, glyceryl methacrylate.

Hydrocolloids from the group of cationic polymers are advantageously chosen for the purposes of the present invention from the group consisting of chitosan, cationic starch derivatives, cationic cellulose derivatives, guar hydroxypropyltrimethylammonium chloride, sodium polystyrenesulfonate.

Particularly advantageous preparations are also obtained when antioxidants are used as additives or active ingredients. According to the invention, the preparations advantageously comprise one or more antioxidants. Antioxidants which are favorable but which are nevertheless optional may be all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, ψ-lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and derivatives thereof and vitamin A and derivatives thereof.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant or antioxidants, the respective concentrations thereof are advantageously chosen from the range 0.001–10% by weight, based on the total weight of the formulation.

If vitamin A or vitamin A derivatives or carotenes or derivatives thereof are used as the antioxidant or antioxidants, the respective concentrations thereof are advantageously chosen from the range 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a coloring action, thickeners, surface-active substances, emulsifiers, emollients, moisturizers and/or humectants, anti-inflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulfates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulfate, zinc sulfate and mixtures thereof.

Corresponding requirements apply mutatis mutandis to the formulation of medicinal preparations.

The W/O emulsions according to the invention can be used as a base for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorocarbons and chlorofluorocarbons (CFCs).

Those cosmetic and dermatological preparations which are in the form of a sunscreen are also favorable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention comprise UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4isopropylbenzyl salicylate, homomenthyl salicylate;

derivatives of benzophenone, preferably 2-hydroxy-4methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminum, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, borage oil or currant seed oil, fish oils, cod-liver oil or also ceramides or ceramide-like compounds etc. It is also advantageous to choose the active ingredients from the group of refatting substances, for example purcellin oil, Eucerit® and Neocerit®.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention without limiting it. The numerical values in the examples refer to percentages by weight, based on the total weight of the respective preparations.

EXAMPLE 1

|  | % by wt. |
|---|---|
| Cetyldimethicone copolymer | 1.0 |
| Isopropyl palmitate | 3.0 |
| Cetiol CC | 4.5 |
| Cyclomethicone | 5.0 |
| Glycerol | 3.0 |
| Chitosan | 0.25 |
| Lactic acid | 0.15 |
| NaCl | 1.0 |
| Perfume, preservative, dyes, antioxidants | q.s. |
| Water | ad 100.0 |

EXAMPLE 2

|  | % by wt. |
|---|---|
| Cetyldimethicone copolymer | 1.5 |
| $C_{12-15}$-Alkyl benzoates | 10.0 |
| Glycerol | 3.0 |
| Sodium polystyrenesulfonate | 1.0 |
| $MgSO_4$ | 0.7 |
| Perfume, preservative, dyes, antioxidants | q.s. |
| Water | ad 100.0 |

EXAMPLE 3

|  | % by wt. |
| --- | --- |
| Cetyldimethicone copolymer | 1.5 |
| Octyl cocoate | 10.0 |
| Glycerol | 3.0 |
| Guar hydroxypropyltrimethylammonium chloride | 1.0 |
| MgSO$_4$ | 0.7 |
| Perfume, preservative, dyes, antioxidants | q.s. |
| Water | ad 100.0 |

EXAMPLE 4

|  | % by wt. |
| --- | --- |
| Cetyldimethicone copolymer | 1.5 |
| Isopropyl stearate | 10.0 |
| Glycerol | 3.0 |
| Sodium polystyrenesulfonate | 0.5 |
| MgSO$_4$ | 0.7 |
| Perfume, preservative, dyes, antioxidants | q.s. |
| Water | ad 100.0 |

EXAMPLE 5

|  | % by wt. |
| --- | --- |
| Cetyldimethicone copolymer | 2.0 |
| Dicaprylyl carbonate | 10.0 |
| Glycerol | 3.0 |
| Sodium chloride | 1.0 |
| Guar hydroxypropyltrimethylammonium chloride | 1.0 |
| Perfume, preservative, dyes, antioxidants | q.s. |
| Water | ad 100.0 |

EXAMPLE 6

|  | % by wt. |
| --- | --- |
| Cetyldimethicone copolymer | 1.5 |
| Dicaprylyl ether | 10.0 |
| Chitosan | 0.25 |
| Salicylic acid | 0.15 |
| Glycerol | 3.0 |
| MgSO$_4$ | 0.7 |
| Perfume, preservative, dyes, antioxidants | q.s. |
| Water | ad 100.0 |

EXAMPLE 7

|  | % by wt. |
| --- | --- |
| Cetyldimethicone copolymer | 1.5 |
| Butylene glycol dicaprylate/dicaprate | 10.0 |
| Glycerol | 3.0 |
| MgSO$_4$ | 0.7 |
| Chitosan | 2.5 |
| Acetic acid | 1.5 |
| Perfume, preservative, dyes, antioxidants | q.s. |
| Water | ad 100.0 |

EXAMPLE 8

|  | % by wt. |
| --- | --- |
| Cetyldimethicone copolymer | 1.5 |
| Dioctylcyclohexane | 10.0 |
| Glycerol | 3.0 |
| MgSO$_4$ | 0.7 |
| Chitosan | 0.25 |
| Citric acid | 0.15 |
| Perfume, preservative, dyes, antioxidants | q.s. |
| Water | ad 100.0 |

What is claimed is:

1. A water in oil emulsion comprising,
   (a) a water phase content of at least 80% by weight based on the total weight of the emulsion,
   (b) a lipid phase wherein the lipid phase comprises at least one lipid selected from the group consisting of isoeicosane, octyl cocoate, neopentyl glycol diheptanoate, propylene glycol dicaprylate/dicaprate, dibutyl adipate, isodecyl neopentanoate, dicaprylyl carbonate, dioctylcyclohexane, dihexyl carbonate, dihexyl ether, cycloparaffin, ethoxy diglycol oleate, ethoxy diglycol, butylene glycol caprylate/caprate, octyl isostearate, decylcocoate, dimethyl isosorbide, wherein the at least one lipid comprises at least 50 wt.-% based on the weight of the lipid phase.
   (c) at least one interface active substance chosen from the group of alkylmethicone copolyols and/or alkyldimeticone copolyols, and
   (d) optionally, at least one viscosity enhancing polymer selected from the group consisting of modified celluloses, acrylate copolymers, acrylatealkylacrylate copolymers, polyethers, vinyl polymers, polysilicic acids, clay minerals, polycarboxylic acids or salts thereof, polyamides and polyimines.

2. The emulsion as claimed in claim 1, wherein the interface-active substance chosen is cetyldimethicone copolyol.

3. The emulsion as claimed in claim 1, wherein the interface-active substance chosen is laurylmethicone copolyol.

4. The emulsion as claimed in claim 1, wherein the total amount of alkylmethicone copolyols and/or alkyldimethicone copolyols is chosen from 0.075 7.5% by weight, based on the total weight of the preparation.

5. The emulsion of claim 1, wherein the total amount of alkylmethicone copolyols and/or alkyldimethicone copolyols is from 0.1 5.0% by weight.

6. The emulsion of claim 5, wherein the total amount of alkylmethicone copolyols and/or alkyldimethicone copolyols is from 1.0 3.0% by weight, based on the total weight of the preparation.

7. The emulsion of claim 1 wherein the at least one lipid comprises at least 80% of the weight of the lipid phase.

8. The emulsion of claim 1 wherein the at less one viscosity enhancing agent is 0.01% to 10% by weight based on the total weight of preparation.

9. The emulsion of claim 1 wherein the at least one lipid comprises at least 80% of the weight of the lipid phase.

10. The emulsion of claim 8 wherein the at least one viscosity enhancing agent is 0.25% to 1% by weight based on the total weight of the preparation.

* * * * *